(12) United States Patent
Herman

(10) Patent No.: US 7,998,410 B2
(45) Date of Patent: Aug. 16, 2011

(54) FULLY CONTINUOUS BIOAEROSOL IDENTIFIER

(75) Inventor: Robert Alan Herman, Baltimore, MD (US)

(73) Assignee: Smiths Detection Inc., Edgewood, MD (US)

( * ) Notice: Subject to any disclaimer, the term of this patent is extended or adjusted under 35 U.S.C. 154(b) by 950 days.

(21) Appl. No.: 10/962,477

(22) Filed: Oct. 13, 2004

(65) Prior Publication Data

US 2005/0084892 A1    Apr. 21, 2005

Related U.S. Application Data

(60) Provisional application No. 60/511,425, filed on Oct. 16, 2003.

(51) Int. Cl.
*G01N 15/06* (2006.01)
*C12Q 1/68* (2006.01)
*C12M 1/00* (2006.01)

(52) U.S. Cl. ........ 422/68.1; 422/82.05; 422/83; 422/88; 435/6; 435/283.1

(58) Field of Classification Search ........................ None
See application file for complete search history.

(56) References Cited

U.S. PATENT DOCUMENTS

| | | | |
|---|---|---|---|
| 4,013,418 A | | 3/1977 | Plakas |
| 5,200,148 A | * | 4/1993 | Saito ................. 422/56 |
| 5,216,925 A | | 6/1993 | Oderheimer |
| 5,508,200 A | * | 4/1996 | Tiffany et al. ............ 436/44 |
| 5,866,430 A | * | 2/1999 | Grow ................. 436/172 |
| 6,363,800 B1 | | 4/2002 | Call et al. |
| 2004/0142338 A1 | * | 7/2004 | Lehmann ................. 435/6 |

FOREIGN PATENT DOCUMENTS

| | | | |
|---|---|---|---|
| DE | 32 01 722 A1 | | 8/1982 |
| DE | 101 62 187 A1 | | 6/2003 |
| GB | 2 251 068 A | | 6/1992 |
| GB | 2 261 949 A | | 6/1993 |
| WO | WO 03/049840 | * | 6/2003 |

* cited by examiner

*Primary Examiner* — Betty Forman
(74) *Attorney, Agent, or Firm* — Casimir Jones, S.C.

(57) ABSTRACT

A system for analyzing a sample includes a strip of material, a first filter for capturing a biological particulate including a nucleic acid, and at least one reagent. Each of the first filter and the reagent are disposed and extend longitudinally on the strip.

25 Claims, 4 Drawing Sheets

FULLY CONTINUOUS BIOAEROSOL IDENTIFIER

CROSS-REFERENCE TO RELATED PATENT APPLICATIONS

This application claims priority to and the benefit of U.S. Provisional Application No. 60/511,425, filed Oct. 16, 2003, and incorporated by reference herein.

BACKGROUND OF THE INVENTION

The present invention relates generally to detection and identification of airborne particles, and, more particularly, to a continuous system for capturing, washing, processing, and analyzing airborne biological particles.

Infectious biological particles such as bacteria and viruses can be transferred from one organism (e.g., a human or animal) to another via an airborne route. For example, biological particles can inadvertently become aerosolized into bioaerosols when a person speaks, coughs, or sneezes or during certain medical and dental procedures that generate particle-containing droplets. Biological particles can also exist, for example, in vaporized water from cooling towers, water faucets, and humidifiers; in agricultural dust; and in other airborne organic materials.

In addition to bioaerosols that are produced inadvertently from common sources, bioaerosols can be generated intentionally. For example, individuals bent on harming others and disrupting society have demonstrated that hazardous biological particles, such as anthrax in micron-sized particles, can be spread in envelopes delivered through the postal system. Such particles can become airborne during processing in postal facilities or when a contaminated envelope is opened. For example, in October 2001, anthrax was discovered in mail processed by the United States Postal Service in Washington, D.C., resulting in serious illness to postal employees and at least two deaths. In October 2001, anthrax was also discovered in the mail room and office buildings of the Unites States Capitol resulting in closure and quarantine of the buildings. Other methods of intentionally distributing and aerosolizing hazardous biological particles include, for example, dispersing particles through ventilation systems or by explosive release.

In order to protect humans and animals from illness caused by inhalation of hazardous bioaerosols, systems to monitor, detect, and identify bioaerosols exist. One commonly used method for monitoring, detecting, and identifying hazardous bioaerosols employs dry filter devices (e.g., air filters) that are manually collected and analyzed using laboratory procedures. The laboratory procedures involve washing the filters using physical agitation, then performing standard laboratory processes (such as centrifuge) to prepare the sample for analysis. Manually collecting and analyzing the filters, however, presents a logistical burden. Moreover, because the collection and analysis systems involve separate components, conventional methods are not well-suited for use in non-laboratory environments. As a result, such systems are not adapted for use by facility security professionals, military forces, and first responders, such as fire fighters, police, emergency medical personnel, and HAZMAT teams, to determine whether a life threatening biohazard is present at locations on-site and in the field.

Although automated collection and identification systems exist, such systems typically employ wet-walled aerosol collectors or similar devices, which require greater amounts of liquid consumables than a dry filter device. For example, wet-walled aerosol collectors and similar devices typically require significant amounts of liquid reagents during a collection cycle in a high temperature environment because the collection fluids evaporate as a result of the high temperature and have to be replenished. Additionally, in low temperature environments, wet-walled aerosol collectors and similar devices require the use of means to prevent the collection fluid or sample air flow from freezing during collection. For example, the collection fluid may be heated. Heating the collection fluid (or employing other means to prevent the collection fluid from freezing), however, imposes additional power requirements on the system.

Another disadvantage of wet-walled aerosol collectors (or similar devices) is that such devices typically have a low retention factor because collected particles re-aerosolize out of the fluid after being collected. As a result, the amount of sample that can be collected over time is reduced.

SUMMARY OF THE INVENTION

According to an embodiment of the present invention, a system for analyzing a sample is provided. The system includes a strip of material, a first filter for capturing a biological particulate including a nucleic acid, and at least one reagent. Each of the first filter and the reagent are disposed and extend longitudinally on the strip.

According to another embodiment, a method for analyzing a sample includes providing a strip of material including a first filter and at least one reagent. Each of the first filter and the reagent are disposed on the strip and extend substantially continuously along a length of the strip. The method also includes placing the strip in a path of a flow of air, capturing a biological particulate in the first filter, subjecting the strip to a wash process to release biological particulate from the first filter into a first liquid sample, subjecting the first liquid sample to a lysis process to release a nucleic acid from the biological particulate, mixing the nucleic acid with the reagent, subjecting the nucleic acid to heating and cooling to amplify the nucleic acid, and analyzing the nucleic acid to determine an identity of the biological particulate.

It is to be understood that both the foregoing general description and the following detailed description are exemplary and explanatory only, and are not restrictive of the invention as claimed.

BRIEF DESCRIPTION OF THE DRAWINGS

The accompanying drawings, which are incorporated in and constitute a part of this specification, illustrate exemplary embodiments of the invention and, together with the description, serve to explain principles of the invention.

DETAILED DESCRIPTION

Figure 1:
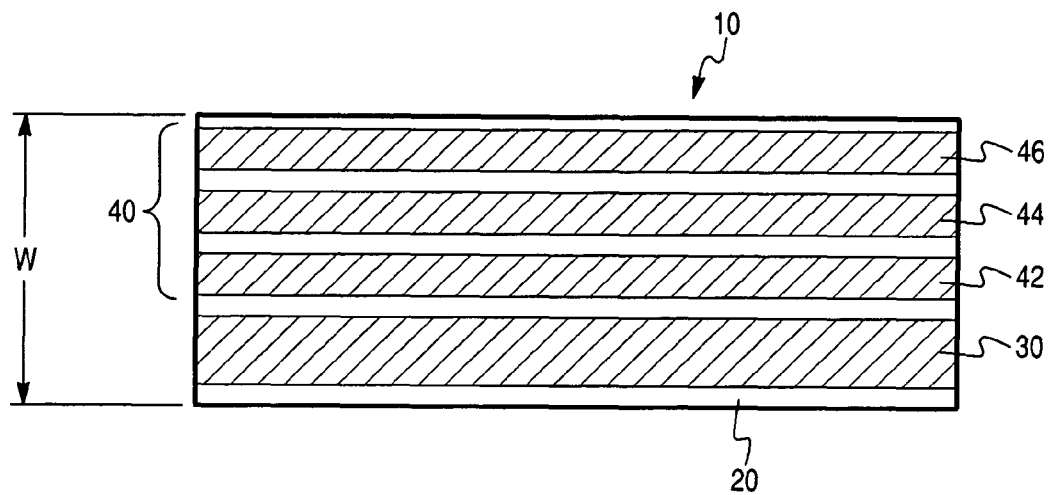
FIG. 1 is a top plan view of an embodiment of a system according to the present invention.
Figure 2:
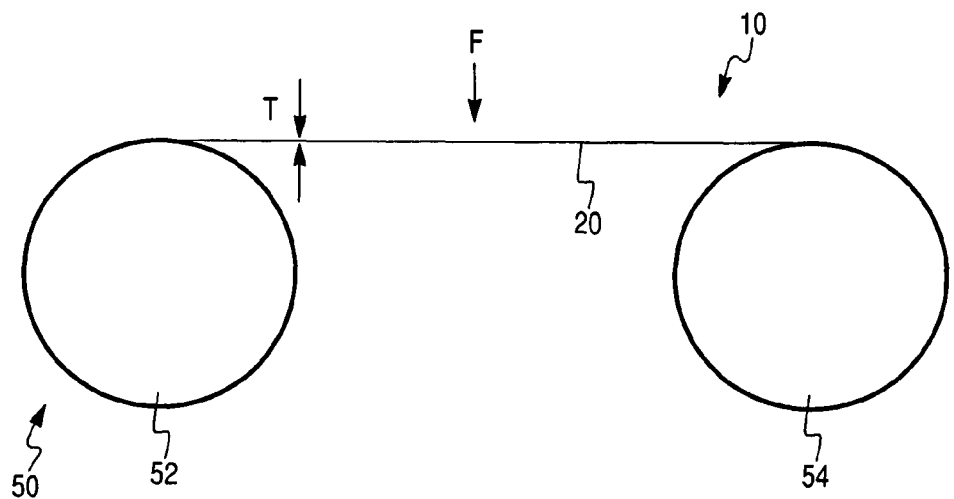
FIG. 2 is a side elevational view of the system of FIG. 1.
Figure 3:
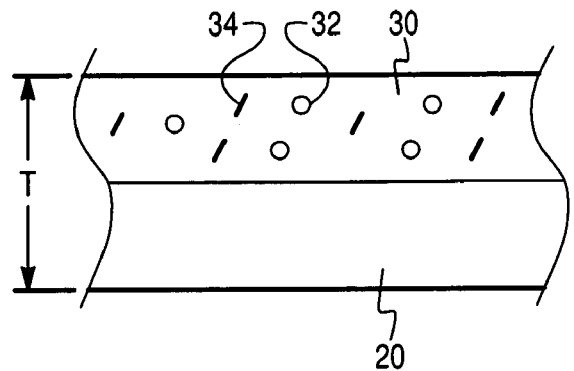
FIG. 3 is a cross sectional side view of a strip of material of the system of FIG. 1 taken along the line 3-3.

FIGS. 1-3 show an embodiment of a system 10 for analyzing a sample according to the present invention. The system 10 includes a strip of material 20, a filter 30, at least one reagent 40, and a cartridge 50.

The strip of material 20 supports the filter 30 and the reagent 40. The strip of material 20 is sufficiently thin and pliable to enable the strip of material 20 to be stored compactly in the cartridge 50. For example, the strip of material 20 may be wrapped about a reel or roller disposed in the cartridge 50. The thickness T and width W of the strip of material 20 may be scaled depending on the size of the filter 30, which is dependent on system performance requirements such as sensitivity. According to one embodiment, the thickness T may be approximately 7 mil, and the width W may be approximately 3 inches. In an exemplary embodiment, the strip of material 20 is substantially continuous in length so that the strip of material 20 may be continuously advanced through the cartridge 50. For example, a length of the strip of material 20 may be approximately 3 feet. The strip of material may be formed from a variety of materials such as composite tape, glass fiber, nitrocellulose, a polypropylene membrane, or a porous membrane (e.g., a TEFLON® porous membrane).

The filter 30 is disposed on the strip of material 20 and extends longitudinally on the strip of material 20, as shown in FIG. 1. In an exemplary embodiment, the filter 30 extends substantially continuously along the length of the strip so that the filter 30 may continuously advance through the cartridge 50 as the strip of material 20 advances through the cartridge 50. To decrease the pressure drop across the filter 30 and improve the efficiency of the collection and/or washing processes, the filter 30 may be integrated on top of the strip of material 20 such that a flow of air F (shown in FIG. 3) only passes through the filter 30. For example, the strip of material 20 may include an aperture or cut-out that aligns with the filter 30 to allow free passage of air. Alternatively, if the strip of material 20 does not have a significant impact on the pressure drop, the materials forming the strip of material 20 and the filter 30 could be sandwiched together to form a composite air filter.

The filter 30 is configured to capture airborne particles, such as airborne biological particulates (i.e., bioaerosols). The filter 30 may be a dry filter device (e.g., an air filter) made of any material capable of collecting micron-sized particles such as cells, spores, viruses, toxins, and/or microorganisms. For example, the filter 30 may be a polyester felt filter, a porous membrane filter, or a glass fiber filter. In an exemplary embodiment, the filter 40 is a polyester felt filter with a 1.0 micron rating. As shown in FIG. 3, particulates 32 become entrained on the filter 30 during a sample collection step in which a flow of air F (shown in FIG. 2) is passed through the filter 30. The particulates 32 may be recovered (washed) from the filter 30 into a liquid sample by any known method, such as percolation (i.e., bubbling or percolating a gas through the filter 30), mechanical agitation, or sonication. The liquid sample may then be subjected to a known lysis process to release nucleic acid such as deoxyribonucleic acid (DNA) from the biological particulate 32.

The filter 30 may optionally include a control agent 34 (shown in FIG. 3). The control agent 34 is embedded in the filter 30 to verify proper operation of the system 10. For example, the control agent 34 may include a fluorescent dye or polystyrene beads with bound DNA segments. When the filter 30 is washed to release the particulate 32, at least a portion of the control agent 34 will also be washed from the filter 30. Thus, the liquid sample generated by washing the filter 30 will include both the particulate 32 the control agent 34. When the liquid sample is analyzed to determine whether a biological particulate is present and to identify the biological particulate, the presence of the control agent 34 in the liquid sample verifies proper washing of the filter 30. In other words, the presence of the control agent 34 confirms that the filter 30 was washed with sufficient force and for a sufficient length of time to release biological particulate 32 trapped in the filter 30. Conversely, an absence of the control agent 34 in the liquid sample indicates that particulate 32 entrained in the filter 30 may not have been washed from the filter 30. Thus, inclusion of the control agent 34 in the filter 30 guards against a false negative reading (i.e., falsely indicating the absence of a biological particle) when the liquid sample is analyzed.

Figure 4:
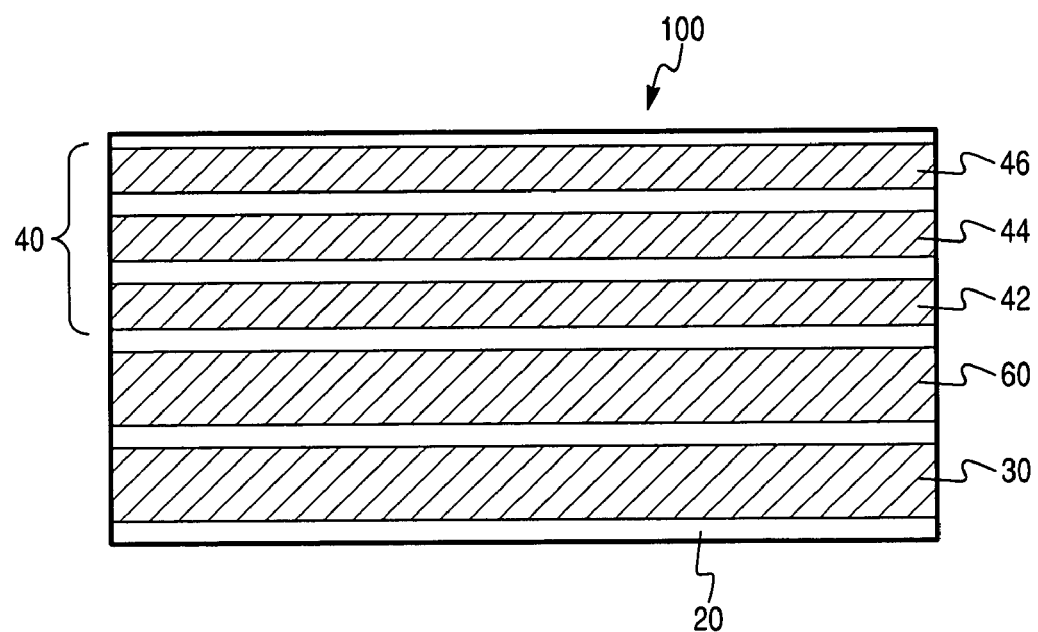
FIG. 4 is a top plan view of another embodiment of a system according to the present invention.

As shown in the embodiment of FIG. 4, a system 100 is identical to the system 10 except the system 100 includes a second filter 60 for capturing nucleic acids that are released from the particulates 32 during the lysis process. The filter 60 is disposed on the strip of material 20 and extends longitudinally on the strip of material 20. In an exemplary embodiment, the filter 60 extends substantially continuously along the length of the strip so that the filter 60 may be continuously advanced through the cartridge 50 as the strip of material 20 advances through the cartridge 50. The second filter 60 may be made of the same material as the strip of material 20. To decrease the pressure drop across the second filter 60 and improve the efficiency of the collection and/or washing processes, the strip of material 20 may include an aperture or cut-out, and the second filter 60 may be disposed on the strip of material 20 so that the second filter 60 aligns with the aperture or cut-out. Alternatively, if the strip of material 20 does not have a significant impact on the pressure drop, the materials forming the strip of material 20 and the filter 60 could be sandwiched together to form a composite filter.

The filter 60 may be made of any material capable of capturing nucleic acid particles. For example, the filter 60 may be a porous membrane filter or a glass fiber filter. In an exemplary embodiment, the filter 60 may be a borosilicate glass fiber filter with a 0.2 μm pore size.

In both of the above-described embodiments, the reagent 40 is disposed on the strip of material 20 and extends longitudinally on the strip of material 20, as shown in FIGS. 1 and 4. In an exemplary embodiment, the reagent 40 extends substantially continuously along the length of the strip of material 20 so that the reagent 40 may be continuously advanced through the cartridge 50 as the strip of material advances through the cartridge 50. The reagent 40 may be, for example, a lyophilized reagent or a reagent otherwise dried onto the strip of material 20. The reagent 40 may include a plurality of reagents. For example, as shown in FIG. 1, the reagent 40 may include a first reagent 42, a second reagent 44, and a third reagent 46. In an exemplary embodiment, the reagent 40 includes all of the components necessary for analysis of the particulates 32. The reagents may be chosen depending upon the application for which the system 10 will be used (i.e., based on the desired tests to be conducted). For instance, in a homeland security application, the reagents may be chosen, as is well known, such that tests are conducted for anthrax, ricin, plague, etc.

The cartridge 50 houses the strip of material 20 of either of the above-described embodiments. The cartridge 50 may be configured to continuously dispense the strip of material 20. The cartridge 50 may also be configured to take up or collect the strip of material 20 after the strip has been dispensed. For example, as shown in FIG. 2, the cartridge 50 may include a first reel 52 and a second reel 54. A first end of the strip of material 20 may be connected to the first reel 52, and a second end of the strip of material 20 may be connected to the second reel 54. When the reels 52, 54 rotate, the strip of material 20 is transferred from the first reel 52 to the second reel 54. In this manner, the strip of material 20 may be dispensed continuously from the cartridge 50 and drawn through an analysis system. A rate of speed at which the strip of material 20 is drawn through the analysis system is dependent upon the application for which the system 10 is being used. Accordingly, the rate of speed will vary and may be readily determined by one of skill so that sufficient particulates 32 are captured on the filter 30, thorough washing of the filter 30 is achieved, thorough DNA capture and extraction are achieved, complete dehydration of reagents is achieved, and sufficient thermal cycling and detection are achieved.

Figure 5:
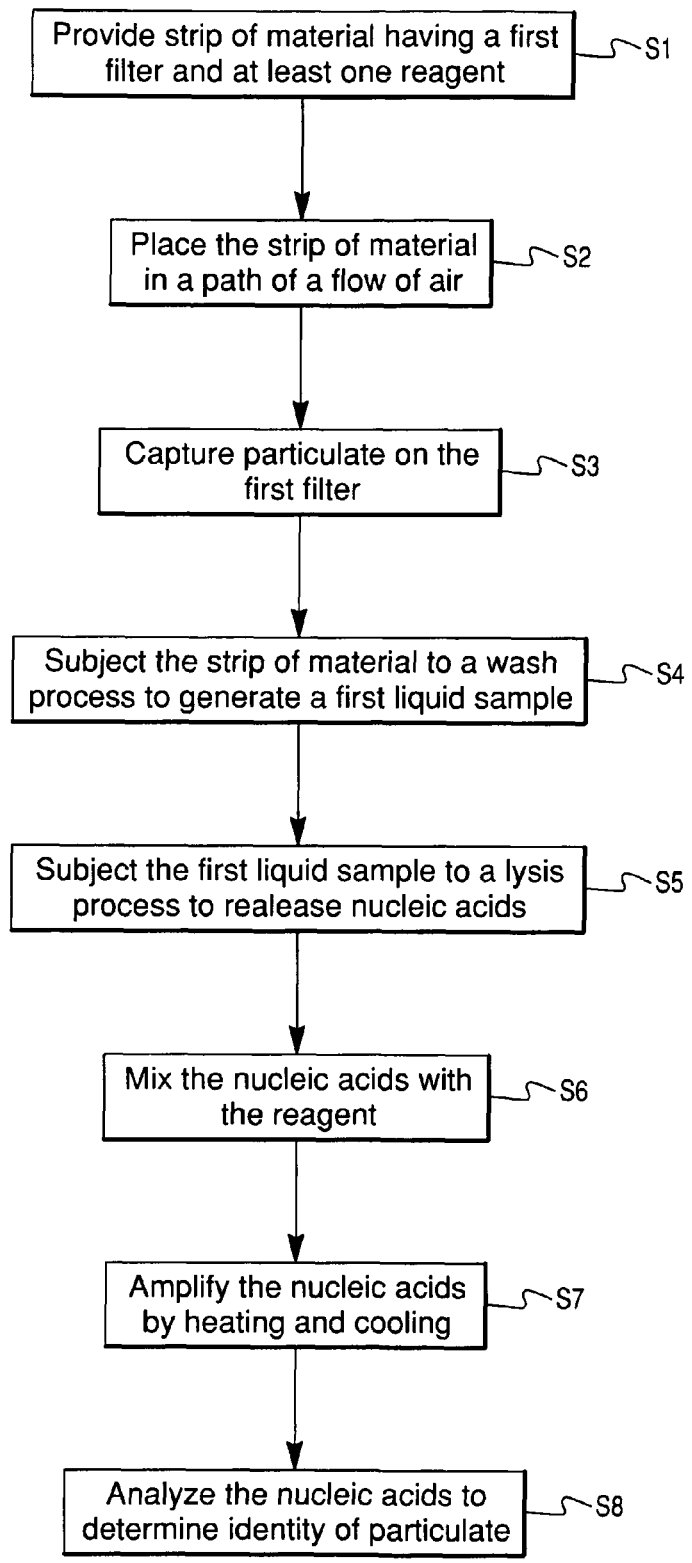
FIG. 5 is a block diagram of an embodiment of a method for analyzing a sample according to the present invention.

In operation, an embodiment of a method for generating and analyzing a sample according to the present invention includes the following steps, as shown in FIG. 5. The steps shown in FIG. 5 may be performed manually by an operator or may be automated. In an exemplary embodiment, the steps shown in FIG. 5 are performed as the strip of material 20 is continuously advanced through an analysis and detection system. In step S1 a strip of material 20 is provided. As discussed above, the strip of material 20 includes a first filter 30 and at least one reagent 40 that are disposed on the strip 20 and extend substantially continuously along a length of the strip 20. In step S2, the strip of material 20 is placed in the path of a flow of air F. In step S3, biological particulates 32 are captured on the first filter 30. In step S4, the strip of material 20 is subjected to a wash process to release the biological particulates 32 from the first filter 30 into a first liquid sample. In step S5, the first liquid sample is subjected to a lysis process to release nucleic acids from the biological particulates 32.

After the nucleic acids are liberated from the particulates 32, the nucleic acids are mixed with the reagent 40 on the strip of material 20 in step S6. If multiple reagents 40 are disposed on the strip 20 (e.g., the first reagent 42, the second reagent 44, and the third reagent 46), the liquid sample is divided into multiple fluid streams. Each fluid stream is them mixed with one reagent on the strip 20. In step S7, the nucleic acids are amplified by subjecting the nucleic acids to heating and cooling (i.e., thermal cycling). In step S8, the nucleic acids are analyzed to determine an identity of the biological particulates 32. The identification step may include any known equipment and processes for performing DNA analysis such as, for example, a flow-through polymerase chain reaction (PCR) process, surface plasmon resonance, and/or a luminometer. In this manner the system 10 may be used to determine whether a life threatening biohazared is present.

Figure 6:
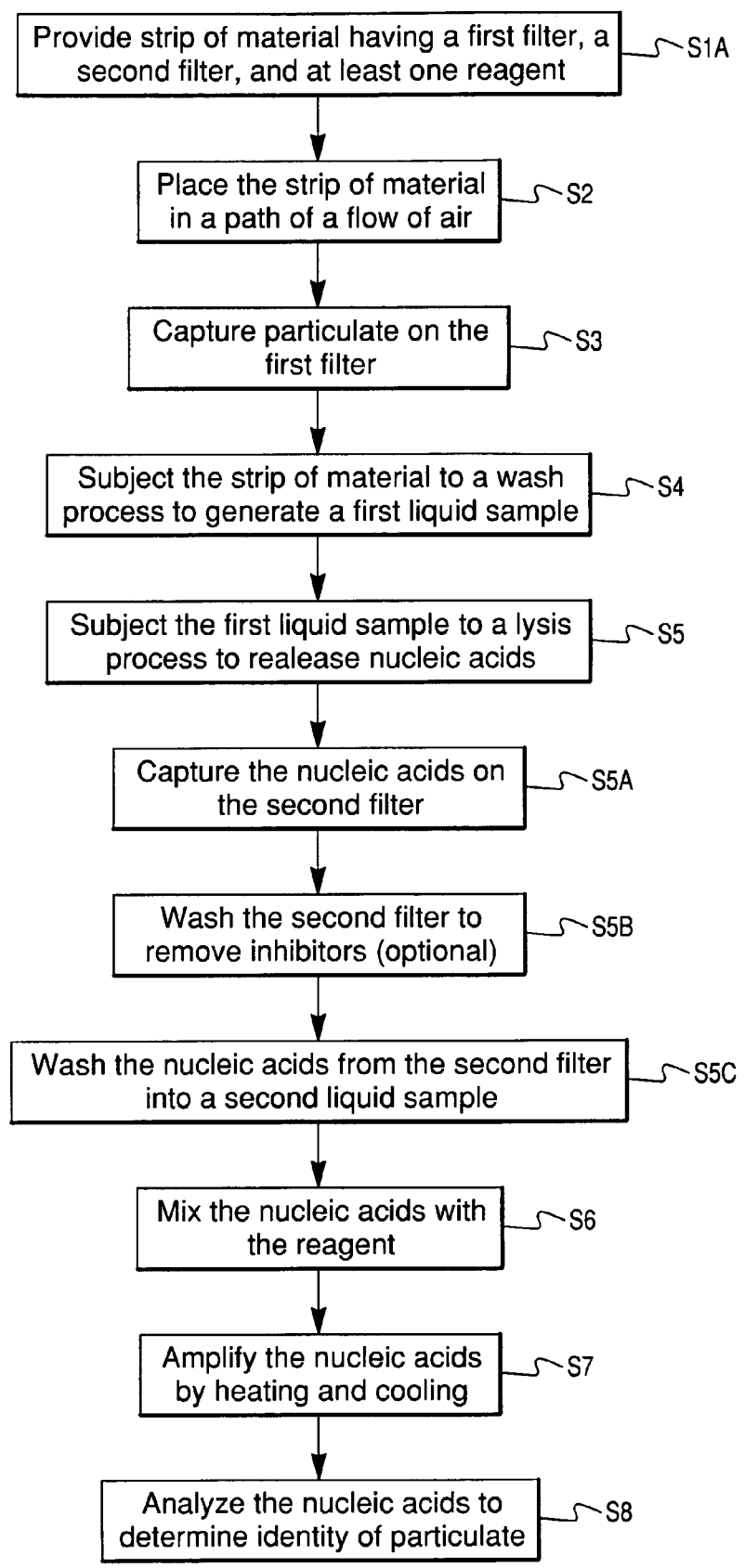
FIG. 6 is a block diagram of another embodiment of a method for analyzing a sample according to the present invention.

Another embodiment of a method for generating and analyzing a sample is shown in FIG. 6. The method of FIG. 6 is identical to the method of FIG. 5 except the method of FIG. 6 includes the use of a second filter 60 (e.g., as shown in FIG. 4) for purification of the first liquid sample. Specifically, in FIG. 6, step S1 is replaced with step S1A in which the strip of material 20 includes the first filter 30, at least one reagent 40, and a second filter 60. As discussed above, the first filter 30, the reagent 40, and the second filter 60 are disposed on the strip 20 and extend substantially continuously along the length of the strip. Steps S2 through S5 are identical to the corresponding steps in FIG. 5. After step S5, however, the method of FIG. 6 includes step S5A. In step S5A, the nucleic acids released in step S5 are captured on the second filter 60. In step S5B, the second filter 60 may optionally be washed to remove any potential inhibitors. In step S5C, the captured nucleic acids are washed from the second filter 60 into a second liquid sample, which has a smaller volume than the first liquid sample. Processing of the nucleic acids continues in steps S6 through S8, which are identical to steps S6 through S8 in FIG. 5. In this manner, the system 100 may be used to determine whether a life threatening biohazard is present.

Thus, according to the above embodiments, the present invention provides a system to enable continuous capture, processing, analysis, and identification of airborne particulates. As a result, collection and analysis procedures may, for example, be automated and integrated into the collection system thereby reducing the logistical burden associated with manually collecting and analyzing the filters. The automated and integrated system may also be suitable for use in non-laboratory environments.

Additionally, the use of a dry filter device as opposed to a wet-walled aerosol collector or similar device has several advantages. For example, fluid evaporation during operation in a high temperature environment may be reduced because the fluid is exposed to the high temperature for a smaller amount of time. Accordingly, less fluid is required for a dry filter device. A dry filter device may also require less power for operation in low temperature environments because the dry filter device does not require the collection fluid to be heated during collection. Moreover, dry filter devices may have a much higher retention factor than wet-walled aerosol collectors or similar devices so that a greater sample volume is collected during a collection period.

Given the disclosure of the present invention, one versed in the art would appreciate that there may be other embodiments and modifications within the scope of the invention. Accordingly, all modifications attainable by one versed in the art from the present disclosure within the scope of the present invention are to be included as further embodiments of the present invention. The scope of the present invention is to be defined as set forth in the following claims.

What is claimed is:
1. A system for analyzing a sample, comprising:
   (a) a strip of material;
   (b) a first dry filter layer for capturing an aerosolized biological particulate, said first dry filter layer disposed and extending longitudinally on the strip; and
   (c) at least one reagent layer different from said first dry filter layer comprising reagent for analysis of the aerosolized biological particulate, said reagent layer disposed and extending longitudinally on the strip,
   wherein the first dry filter layer and the reagent layer extend substantially continuously along the length of the strip, and
   wherein the aerosolized biological particulate comprises a nucleic acid.

2. The system of claim 1, wherein the aerosolized biological particulate is selected from the group consisting of cells, spores, viruses, toxins, and microorganisms.

3. The system of claim 1, wherein the first dry filter layer includes a dry air filter layer.

4. The system of claim 1, wherein the first dry filter layer includes polyester felt.

5. The system of claim 1, wherein the first dry filter layer includes a control agent to verify proper washing of the dry filter.

6. The system of claim 5, wherein the control agent includes polystyrene beads with bound deoxyribonucleic acid segments and/or a fluorescent dye.

7. The system of claim 1, wherein the strip is in contact with the first dry filter layer and the first dry filter layer is in contact with the reagent layer.

8. The system of claim 1, further comprising a second dry filter for capturing the nucleic acid, wherein the second dry filter is disposed and extends longitudinally on the strip.

9. The system of claim 8, wherein the second dry filter is a porous membrane filter or a glass fiber filter.

10. The system of claim 8, wherein the first dry filter, the second dry filter, and the reagent extend substantially continuously along a length of the strip.

11. The system of claim 1, wherein the material includes composite tape.

12. The system of claim 1, wherein the material includes a porous membrane.

13. The system of claim 1, wherein the material includes glass fiber.

14. The system of claim 1, wherein the material includes polypropylene membrane.

15. The system of claim 1, wherein the material includes nitrocellulose.

16. The system of claim 1, wherein the reagent includes a lyophilized reagent.

17. The system of claim 1, further comprising a cartridge that includes first and second reels, wherein a first end of the strip is connected to the first reel and a second end of the strip is connected to the second reel.

18. The system of claim 17, wherein the first and second reels are configured to rotate to transfer the strip of material from the first reel to the second reel.

19. A method for analyzing a sample, comprising:
providing the system of claim 1;
placing the strip in a path of a flow of air;
capturing a biological particulate in the first filter;
subjecting the strip to a wash process to release biological particulate from the first filter into a first liquid sample;
subjecting the first liquid sample to a lysis process to release a nucleic acid from the biological particulate;
mixing the nucleic acid with the reagent;
subjecting the nucleic acid to heating and cooling to amplify the nucleic acid; and
analyzing the nucleic acid to determine an identity of the biological particulate.

20. The method of claim 19, wherein the strip of material includes a second filter disposed on the strip and extending substantially continuously along the length of the strip.

21. The method of claim 20, after the step of subjecting the first liquid sample to a lysis process to release a nucleic acid from the biological particulate and before the step of mixing the nucleic acid with the reagent, further comprising:
capturing the nucleic acid in the second filter; and
washing the captured nucleic acid from the second filter into a second liquid sample of smaller volume than the first liquid sample.

22. A system for analyzing a sample, comprising:
(a) a strip of material;
(b) a first dry filter layer for capturing an aerosolized biological particulate, said dry filter having a first major surface and a second major surface opposite the first major surface, said first major surface adjacent to a first major surface of the strip; and
(c) a reagent layer comprising at least one reagent for analyzing the biological particulate, said reagent layer having a first major surface adjacent to the second major surface of the first dry filter.

23. The system of claim 22, wherein the aerosolized biological particulate comprises a nucleic acid.

24. The system of claim 22, wherein the first major surface of the dry filter layer is in contact with the first major surface of the strip.

25. The system of claim 22, wherein the first major surface of the reagent layer is in contact with the second major surface of the dry filter.

* * * * *